(12) United States Patent
Alqahtani

(10) Patent No.: US 10,729,850 B1
(45) Date of Patent: Aug. 4, 2020

(54) MODULAR DENTAL MATERIAL DISPENSER

(71) Applicant: KING SAUD UNIVERSITY, Riyadh (SA)

(72) Inventor: Shafia Abdullah Alqahtani, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/684,732

(22) Filed: Nov. 15, 2019

(51) Int. Cl.
| A61C 19/02 | (2006.01) |
| A61M 5/19 | (2006.01) |
| A61C 19/00 | (2006.01) |
| A61M 5/31 | (2006.01) |
| A61M 5/00 | (2006.01) |
| B65D 21/02 | (2006.01) |

(52) U.S. Cl.
CPC ............... *A61M 5/19* (2013.01); *A61C 19/00* (2013.01); *A61M 5/008* (2013.01); *A61M 5/3129* (2013.01); *B65D 21/0209* (2013.01); *A61M 2005/3131* (2013.01)

(58) Field of Classification Search
CPC ........ A61M 2005/3142; A61M 5/1413; A61M 2005/14268; A61M 2005/005; A61M 5/008; A61M 5/002; A61M 5/19; A61M 5/53129; A61M 2005/3131; A61C 19/00; A61C 19/02; B65D 21/0209; B35D 83/0005; B05C 17/01
USPC ....... 206/368, 369, 63.5, 503; 222/325, 326, 222/386, 143
See application file for complete search history.

(56) References Cited

U.S. PATENT DOCUMENTS

| 4,995,540 A | 2/1991 | Colin et al. |
| 5,277,332 A | 1/1994 | Rogers |
| 5,871,355 A | 2/1999 | Dragan et al. |
| 6,099,306 A | 8/2000 | Lawler |
| 6,540,072 B1 | 4/2003 | Fischer |
| 6,929,157 B2 | 8/2005 | Orecchia et al. |
| 7,341,452 B2 | 3/2008 | Dragan et al. |
| D602,593 S | 10/2009 | Cheetham |
| 2004/0033466 A1 | 2/2004 | Shellard et al. |
| 2004/0074795 A1* | 4/2004 | Fischer .................. A61C 19/02 206/366 |
| 2006/0116646 A1 | 6/2006 | Weiss |
| 2010/0175348 A1* | 7/2010 | Fundingsland .......... A61C 5/62 53/111 R |
| 2012/0160718 A1 | 6/2012 | Yamaguchi et al. |
| 2016/0137345 A1* | 5/2016 | Grodsky ............ B65D 21/0209 222/143 |

FOREIGN PATENT DOCUMENTS

GB       1060361 A    3/1967

* cited by examiner

*Primary Examiner* — Heidi M Eide
(74) *Attorney, Agent, or Firm* — Richard C. Litman; Nath, Goldberg & Meyer

(57) ABSTRACT

A modular dental material dispenser can include multiple stackable, modular components, each having a syringe extending therethrough. The syringe of each component may include a detachable nozzle attachment to assist in efficiently dispensing the materials contained therein. Two or more modular components may be connected to provide a dispenser capable of dispensing multiple materials using different dispensing nozzles.

4 Claims, 2 Drawing Sheets

MODULAR DENTAL MATERIAL DISPENSER

BACKGROUND

1. Field

The present disclosure relates to dental devices, and in particular, to a modular, multiple syringed dental material dispenser.

2. Description of the Related Art

Many modern dental procedures require different materials to be dispensed into a patient's mouth throughout the procedure. For example, a practitioner may prepare a surface of a tooth for bonding using an acid etch solution. The acid etch solution dissolves some of the enamel and dentine to create a surface that better absorbs a bonding agent. Then, the practitioner typically applies a bonding agent to the etched tooth, followed by a dental restorative material on top of the bonding agent to provide a fully restored tooth.

In many cases, the materials are dispensed in consecutive steps. Switching between different dispensers for each material may extend the duration of the procedure and increase the chance of error. Thus, a dental material dispenser solving the aforementioned problems is desired.

SUMMARY

A modular dental material dispenser can include multiple stackable, modular components, each having a syringe extending therethrough. Each syringe may be filled with a different material. A detachable nozzle attachment, such as a needle attachment or a brush attachment, may be attached to each syringe to assist in efficiently dispensing the material therein. Two or more modular components may be detachably connected to provide a dispenser capable of dispensing multiple materials.

The modular dental material dispenser may be provided in a kit having multiple modular components that may be assembled as desired by a user. The kit may also include nozzle attachments.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
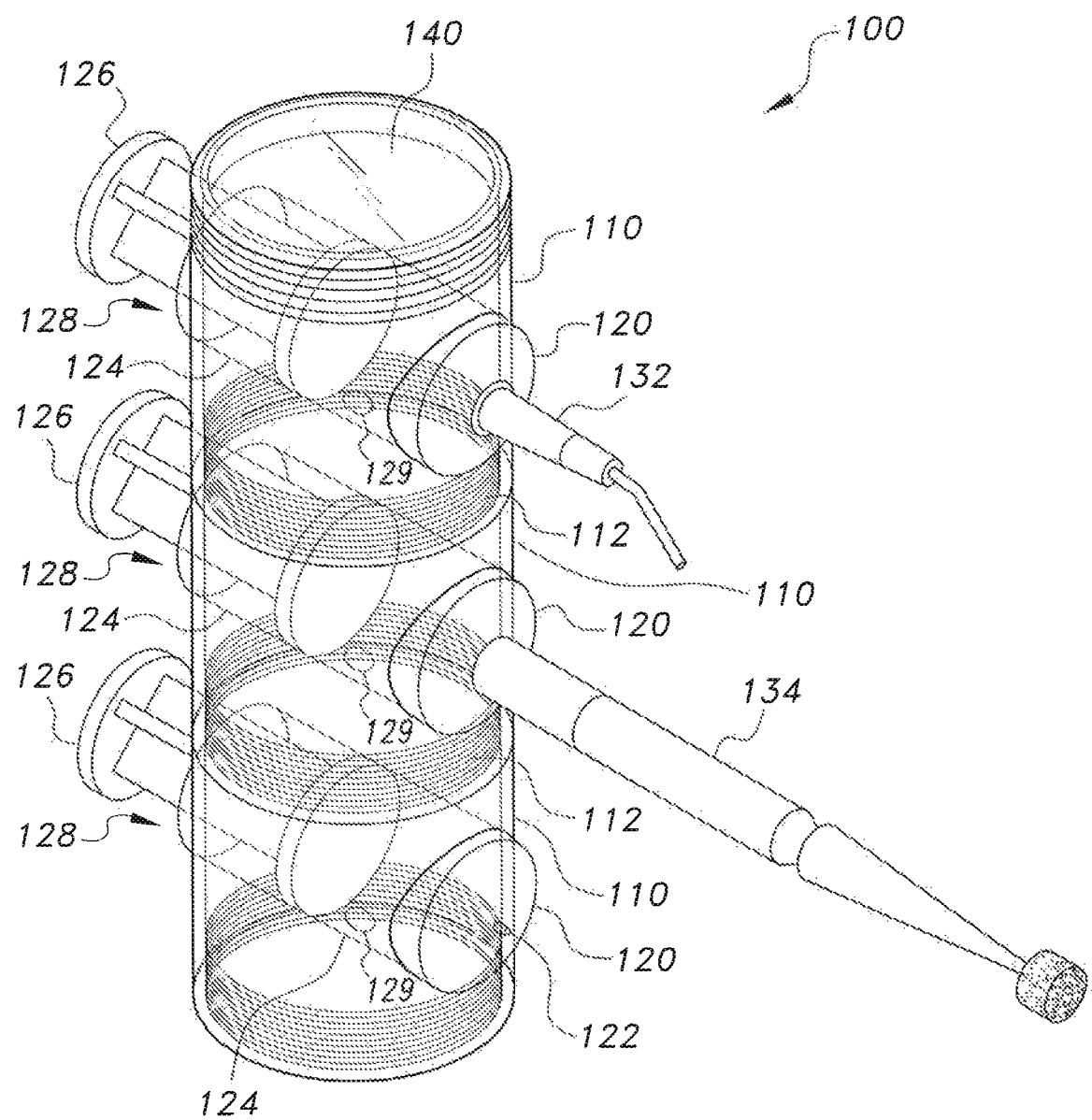
FIG. 1 is a perspective view of a modular dental material dispenser having multiple syringes.

FIG. 1 shows an embodiment of a modular dental material dispenser 100 including a plurality of stacked modular components 110. In some embodiments, each modular component 110 threadedly engages an adjacent modular component 110. Each modular component 110 includes threads 112, a syringe 120 having a barrel 124, a plunger 126, a nozzle 122, and sealable side aperture 129. Nozzle attachments 132, 134 may be provided for connection to the nozzles 122 based on the material being dispensed and the procedure of applying the material. For example, an upper syringe 120 may be filled with an acid etching solution, a middle syringe 120 may be filled with a dentine bonding agent, and a lower syringe 120 may be filled with a dental restorative material. Accordingly, the upper syringe 120 may have a needle attachment 132 attached to the nozzle 122 for accurately administering the less viscous acid etch material, the middle syringe 120 may include a brush attachment 134 for evenly spreading the dentine bonding agent around the surface of a tooth, and the lower syringe 120 may not include a nozzle attachment since the restorative material may have a high viscosity that is easily applied via the syringe nozzle 122. Once the modular components 110 are assembled, a cap 140 may be removably attached to the upper end of the upper most modular component 110. In some embodiments, the dispenser 100 may include 2 to 5 modular components.

In some embodiments, the syringes 120 of different modular components 110 may have different sizes. For example, some procedures may require a different amount of each material amount, which may be accommodated by combining modular components 110 having different sized syringes 120. Smaller syringes 120 may be provided in smaller modular components 110, thus reducing the overall size of the dispenser 100. In addition, syringes 120 having smaller diameter barrels 124 allow for more precise dispersion of the material therein. Accordingly, modular components 110 having smaller diameter barrels 124 may be added to the dispenser 100 for procedures that require high precision material dispensing.

Figure 2:
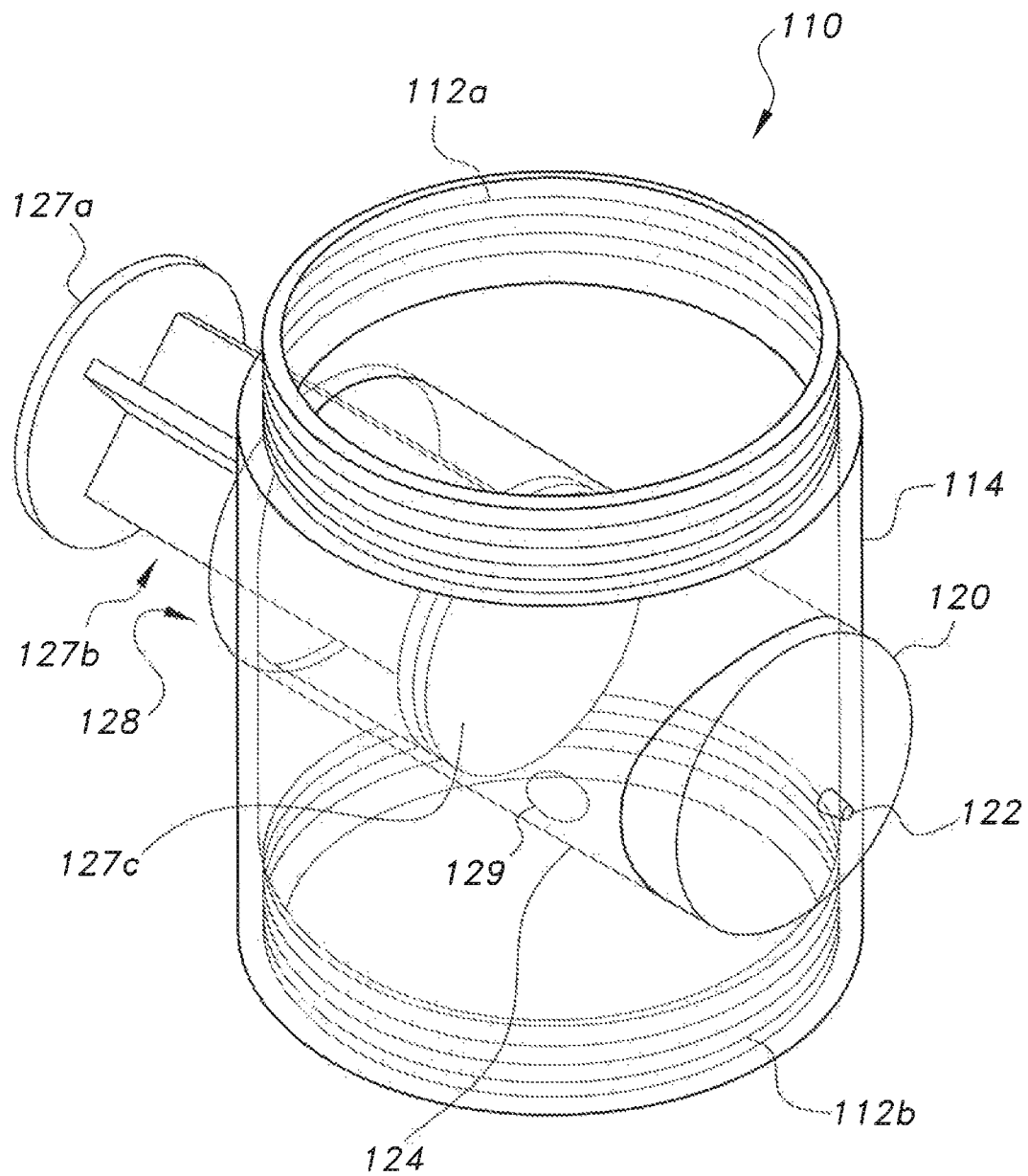
FIG. 2 is a perspective view of a modular component of the dispenser of FIG. 1.

FIG. 2 shows an embodiment of the modular component 110. The modular component 110 includes a tubular body 114. A top end of the body 114 may define an outward facing thread pattern 112a and a lower end of the body 114 may define an inward facing thread pattern 112b configured to threadingly engage with the upper thread pattern 112a of an adjacent modular component 110. Although thread patterns are shown, it should be understood that the modular components 110 may be attached together by snap fit connection or other suitable means. The syringe 120 may extend through the body 114, with the nozzle 122 extending out of one side of the body 114, and a plunger accepting opening 128 extending out of an opposing side of the body 114. The syringe 120 may be integrally formed with the body 114 or it may be a separate component inserted into an opening defined by the body 114. The plunger 126 includes a disc-shaped head 127a, a flat end 127c, and an elongated intermediate portion 127b extending between the head 127a and the end 127c. The head 127a can have a diameter that is at least as large as a diameter of the barrel 114 and may be pressed to dispense material from the barrel 124. A material can be loaded into the barrel 124 through the sealable opening 129 prior to assembling the components 110 together.

Components of the material dispenser 100 may be provided in a kit. The kit may include multiple modular components 110 and multiple nozzle attachments 132, 134. The nozzle attachments 132, 134 may have different sizes. In some embodiments, the syringes 120 in the kit may be prefilled with materials such as acid sketch solutions, dentine bonding agents, and/or dental restorative materials that are known in the art.

The body 114, barrel 124, nozzle 122, and plunger 126 may all be made of a suitable polymer, such as polypropylene. The head 126a of the plunger may be made of, or coated in silicone or rubber. The body 114 and barrel 124 may be made of a clear material, as shown in the figures, to provide visual access to the material within the syringe 120. In some embodiments, the syringe barrel 124 may include markers along its length to indicate the amount of material within the barrel 124.

It is to be understood that the modular dental material dispenser is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A modular dental material dispenser having multiple syringes, comprising:

at least two modular components threadedly detachably connected together in a vertical direction, each modular component consisting of:

a tubular body having opposing open ends, the opposing ends being configured for threadedly detachable connection to a tubular body of another modular component;

a syringe barrel integrally formed with and extending through the tubular body, the syringe barrel defining a nozzle at one end and a plunger accepting opening at an opposite end, wherein the syringe barrel further includes a sealable side opening; and a plunger disposed within the syringe barrel.

2. The modular dental material dispenser of claim 1, wherein the nozzle of the syringe barrel is detachably connected to a nozzle attachment selected from the group consisting of a needle and a brush.

3. The modular dental material dispenser of claim 1, wherein the plunger includes a disk shaped head having a diameter that is at least the same as a diameter of the syringe barrel.

4. The modular dental material dispenser of claim 1, further comprising a cap threadedly detachably connected to one of the modular components.

* * * * *